(12) United States Patent  (10) Patent No.: US 7,982,876 B2
Haugholt et al.  (45) Date of Patent: Jul. 19, 2011

(54) APPARATUS AND METHOD FOR INSPECTING A STREAM OF MATTER BY LIGHT SCATTERING INSIDE THE MATTER

(75) Inventors: Karl Henrik Haugholt, Olso (NO); Ib-Rune Johansen, Oslo (NO); Jon Tschudi, Oslo (NO); Erik Wold, Oslo (NO); Jens Petter Wold, As (NO); Alain Ferber, Haslum (NO)

(73) Assignee: TiTech Visionsort AS, Oslo (NO)

( * ) Notice: Subject to any disclaimer, the term of this patent is extended or adjusted under 35 U.S.C. 154(b) by 737 days.

(21) Appl. No.: 11/587,864

(22) PCT Filed: Apr. 28, 2005

(86) PCT No.: PCT/GB2005/001660
§ 371 (c)(1),
(2), (4) Date: Aug. 10, 2007

(87) PCT Pub. No.: WO2005/106438
PCT Pub. Date: Nov. 10, 2005

(65) Prior Publication Data
US 2008/0018892 A1    Jan. 24, 2008

(30) Foreign Application Priority Data
Apr. 30, 2004  (GB) .................................. 0409691.3

(51) Int. Cl.
*G01N 21/00* (2006.01)
(52) U.S. Cl. ........................................ 356/338; 356/431
(58) Field of Classification Search .......... 356/429–431, 356/237.1–237.2, 239.4, 240.1, 601, 613, 356/625, 628, 445–448, 337–343; 209/576–577, 209/580, 587–588, 639, 936, 938; 250/301, 250/225, 223, 223.12, 559.11, 559.16
See application file for complete search history.

(56) References Cited

U.S. PATENT DOCUMENTS

| | | | | |
|---|---|---|---|---|
| 4,352,430 A * | 10/1982 | Maier et al. | .................... | 209/577 |
| 4,629,319 A * | 12/1986 | Clarke et al. | ................ | 356/237.2 |
| 4,998,824 A * | 3/1991 | Littlejohn et al. | ............ | 356/407 |
| 5,383,135 A * | 1/1995 | Shofner et al. | ................. | 700/143 |
| 5,419,438 A * | 5/1995 | Squyres et al. | ................ | 209/3.1 |
| 6,864,970 B1 * | 3/2005 | Ruymen et al. | ............ | 356/237.1 |
| 2006/0108346 A1 * | 5/2006 | Janhunen | ...................... | 219/388 |

* cited by examiner

*Primary Examiner* — Tarifur Chowdhury
*Assistant Examiner* — Michael LaPage
(74) *Attorney, Agent, or Firm* — Calfee, Halter & Griswold LLP

(57) ABSTRACT

A system (10) for automatically inspecting a stream of matter (12) for varying composition, comprising an emitting device (16) serving to emit a detection medium, which comprises electromagnetic radiation of a substantially constant intensity, to an irradiated zone (I) of the stream at which the medium penetrates a surface of the matter (12), the irradiated zone (I) extending continuously across substantially the width of the stream, the medium penetrating the surface being varied by the matter (12), a receiving device (32) for receiving the varied medium emanating from the matter (12) at a detection zone (D) substantially separate from the irradiated zone (I), and a detecting device (34) serving to generate detection data in dependence upon the varied medium, the arrangement being such that, in use of the system (10), at least the majority of the varied medium received at the receiving device (32) can be transflected medium.

46 Claims, 3 Drawing Sheets

Figure 1:
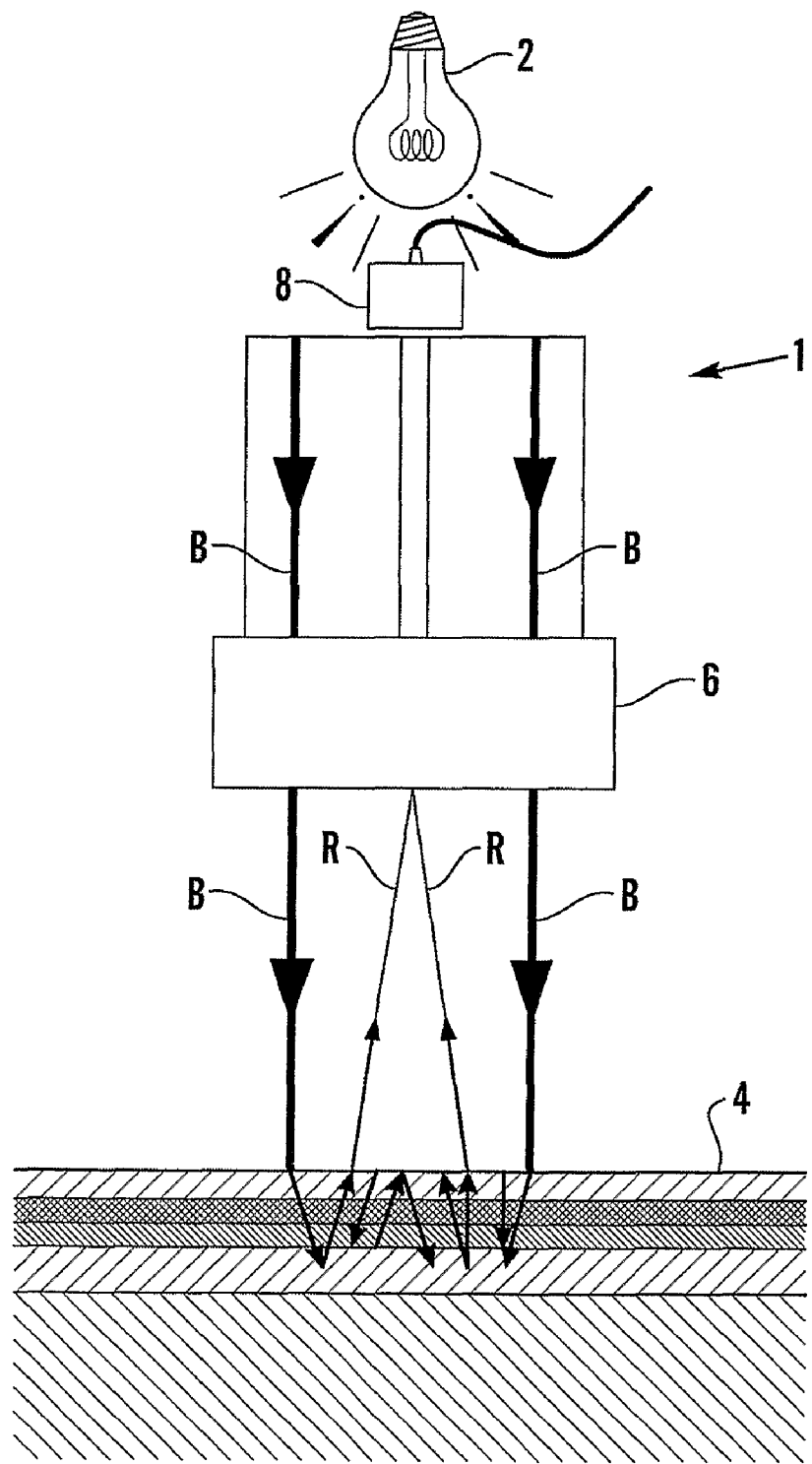

APPARATUS AND METHOD FOR INSPECTING A STREAM OF MATTER BY LIGHT SCATTERING INSIDE THE MATTER

This invention relates to automatically inspecting matter, for instance the automatic inspection and sorting of discrete objects for quality and/or differing composition.

U.S. Pat. No. 5,419,438 discloses a sorting apparatus which includes a conveyor belt for carrying a stream of randomly-arranged articles, at least some of which are post-consumer plastics articles made of polyvinyl chloride (PVC) and others which are made of polyethylene terephthalate (PET). The conveyor belt carries the articles to an irradiation area where they are irradiated with ultraviolet light that induces the post-consumer articles of PVC to emit phosphorescent light that persists after the irradiation ends. The conveyor belt then carries the articles to an inspection zone that is isolated from the ultraviolet light. A video camera is positioned to receive phosphorescent light emitted from post-consumer articles made of PVC. Other articles commonly in the stream of post-consumer plastics articles (for example, PET) do not emit phosphorescent light and are, therefore, distinguishable from the PVC articles.

EP-A-341096 discloses a method of separating diamonds from gangue, in which particles of the gangue are carried along a belt and are irradiated with a beam from a laser. The luminescence emitted by the particles is then detected by two spaced-apart optical modules. The difference in the luminescence detected is related to the nature of the material, and a simple microprocessor and ejection jet can be used to eject diamonds into a sort bin.

U.S. Pat. No. 3,356,211 discloses a system for the separation of ore particles preferentially coated with liquid fluorescent material. A desired mineral may be separated from a worthless portion by radiating the ore to cause a portion of it to emit at a characteristic wavelength and sensing the emitted rays. The sensed rays are used to operate means for separating the ore into a desired and an undesired portion. The desired separation may be achieved by first treating a quantity of the ore with a liquid which preferentially coats the particles of one of the portions of the ore and is also capable of emitting at a characteristic wavelength upon exposure to ultraviolet light, X-rays, or other suitable type of electromagnetic radiation. The treated ore is then passed to a separation zone where an electromagnetic wave means sensitive to the characteristic wavelength detects which particles are coated and which particles are not. The sensing means then functions to actuate a deflecting means which physically removes the coated particles from the body of ore particles. The coating may be dispensed with in the case of natural fluorescing ores.

GB-A-2188727 discloses a system for sorting ore particles by subjecting them to electromagnetic radiation in the microwave part of the spectrum, the frequency of the radiation being at the resonant frequency of water or that of one or more target minerals or possibly a combination of such frequencies. The resultant heat emission characteristics of the particles are deflected by, for example, an infra-red detector and subsequently analysed. Particles exhibiting a desired heat emission characteristic are separated from other particles which do not exhibit such characteristic.

U.S. Pat. No. 5,894,345 discloses an optical system of detecting defects in the form of cracks in a ceramic substrate or sintered metal product and comprises a light source for emitting light beams for illuminating an object so that the light beams form a dotted line on the object, the light beams being aimed at the surface of the object so that their intensities differ from each other at the surface. The system further comprises a measuring arrangement which measures changes in the intensity of light which is emitted from the surface of the inspected object and which has entered and passed partly through the object.

According to one aspect of the present invention, there is provided apparatus for automatically inspecting a stream of matter for varying composition, comprising an emitting device serving to emit a detection medium, which comprises electromagnetic radiation of a substantially constant intensity, to an irradiated zone of said stream at which said medium penetrates a surface of said matter, said irradiated zone extending continuously across substantially the width of said stream, said medium penetrating said surface being varied by said matter, a receiving device for receiving the varied medium emanating from said matter at a detection zone substantially separate from said irradiated zone, and a detecting device serving to generate detection data in dependence upon said varied medium, the arrangement being such that, in use of said apparatus, at least the majority of said varied medium received at said receiving device can be transflected medium.

According to a second aspect of the present invention, there is provided a method of automatically inspecting a stream of matter for varying composition, comprising emitting a detection medium, which comprises electromagnetic radiation of a substantially constant intensity, so as to irradiate a zone of said stream, which zone extends continuously across substantially the width of said stream, penetrating a surface of said matter with said detection medium at the irradiated zone, wherein said medium is varied by said matter, receiving at a receiving device the varied medium emanating from said matter, at least the majority of said varied medium received at said receiving device being transflected medium, and generating detection data in dependence upon said varied medium.

Owing to these two aspects, the stream of matter can be relatively wide, thereby enabling a relatively high inspection rate and thus a relatively high measuring capacity.

Advantageously, by applying multiple sensors and/or a scanning system, it becomes possible to introduce a large number of detection points.

The detection medium can be electromagnetic radiation, for example infra-red, to detect variations in the stream of matter, for example in the quality of food products. In order for the automatic inspection to take place most effectively, the matter should be distributed in the stream in a substantially single layer.

Preferably, the matter is advanced through the irradiated and detection zones on a conveyor belt. Alternatively, the matter can be advanced through the irradiated and detection zones on a vibrating table.

Advantageously, the detection zone is substantially separated from the irradiated zone by a shielding device, for example in the form of a screen, which prevents stray or directly reflected radiation from reaching the detecting device and causing erroneous detection data.

The emitting device is, preferably, a row of lamps such that the irradiated zone is an illuminated zone, the illumination of the irradiated zone being to a degree which is greater than that of the background illumination which may be present at the detection zone.

Preferably, the emitting device and the receiving device are located on the same side of the matter.

What is meant by transflection of the medium is that the emitted medium penetrates into the matter and is then scattered by the matter, and the scattered medium then emanates from the matter as transflected medium to be received at the receiving device substantially simultaneously with the irradiation, so that the latter device receives only that medium that has passed into and has been scattered by the matter. In particular, the transflected medium is that medium which has passed through a portion of the matter and has been scattered by the internal structure of the matter. The transflected medium is also of the same wavelength range as that of the emitted medium.

Transflection is a useful technique for measuring quality of the matter, for example food, by measuring parameters such as water content, protein content and sugar and carbohydrate content. Transflection is also useful for the measurement of sub-surface characteristics and/or defects in the product, such as fish or meat, or in other applications that require measuring sub-surface characteristics. Examples of such characteristics can be local inhomogenities and anisotropics in the material structure. In relation to the measuring of food quality, and in particular to fish, split cod, (i.e. salted dried cod) is an industrial product of Norway. Customer acceptance and the price depends on the water content being below an allowed limit. Water content estimation is thus critical in production and this is usually determined by skilled workers known as graders who manually assess the water content. Split cod normally has a water content in the range of 40-50% and automatic inspection and sorting of the different qualities will improve the production process by improving the precision and repeatability of reliable inspection. Water has strong spectral features in the wavelength range 900 nm to 1500 nm. If the stream moves at a speed of between 1 and 2 metres per second, and a suitable scanning arrangement is used, the water content of each split cod passing through the detection zone can be determined in less than 1 second.

Another useful measurement which can be determined using transflected medium is the fat content of animal tissue, for example, the fat content of meats and fish. Furthermore, transflected medium can be used to detect the possible presence of contaminating foreign bodies in fish roe to be sold for human consumption.

The radiation that enters the matter undergoes multiple scattering caused by internal structures in the body of the matter, and some of the varied radiation is eventually scattered back out of the matter and it is this varied radiation which is used for analysis. The amount of varied medium scattered back out of the matter is usually very small owing to transmission and reflection losses and to absorption by the matter, so that reliable measurement can be difficult. The path of the radiation whilst inside the matter may be completely random.

In order that the invention may be clearly and completely disclosed, reference will now be made, by way of example, to the accompanying drawings, in which:—

Figure 2:
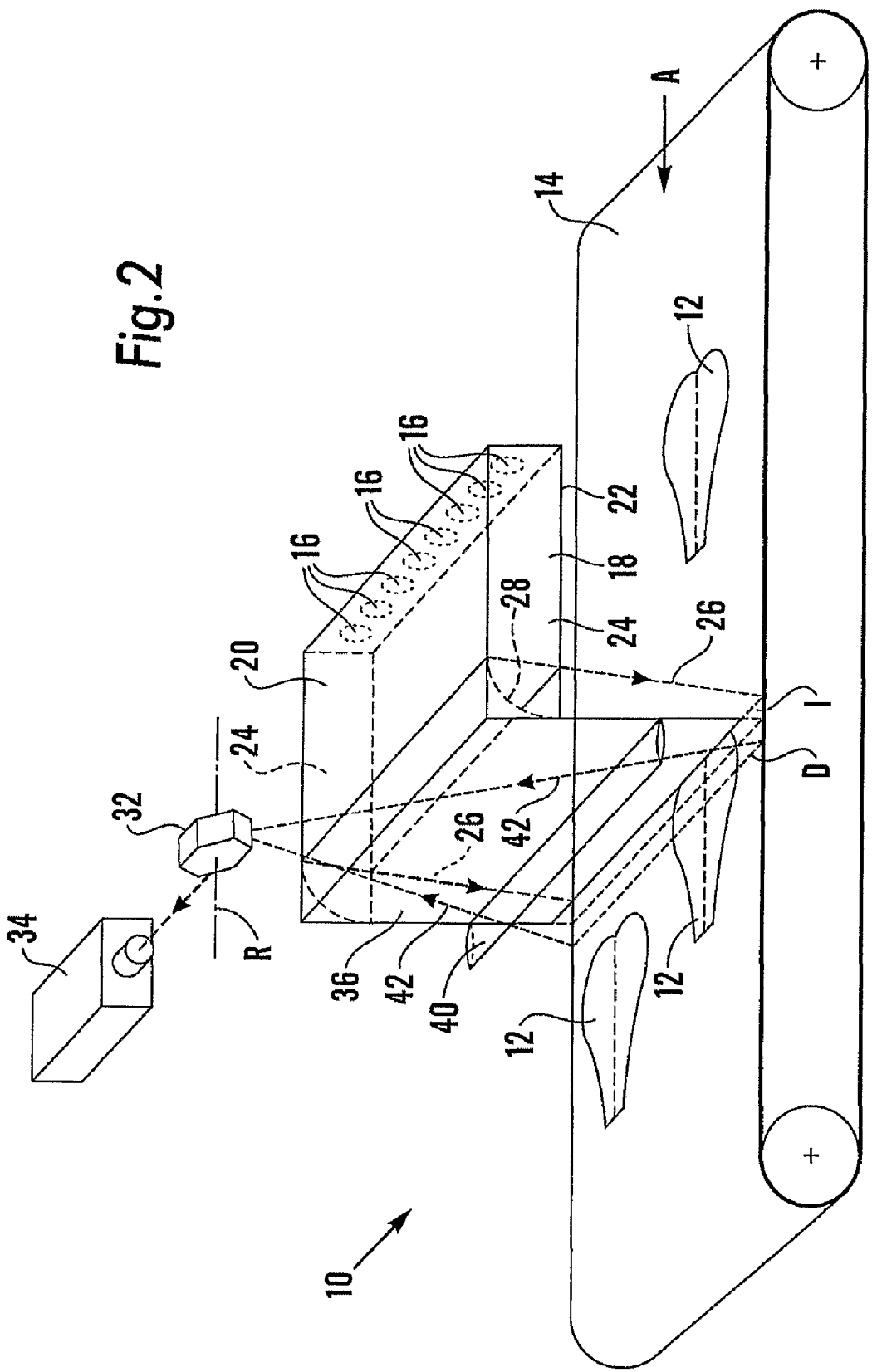
Figure 3:
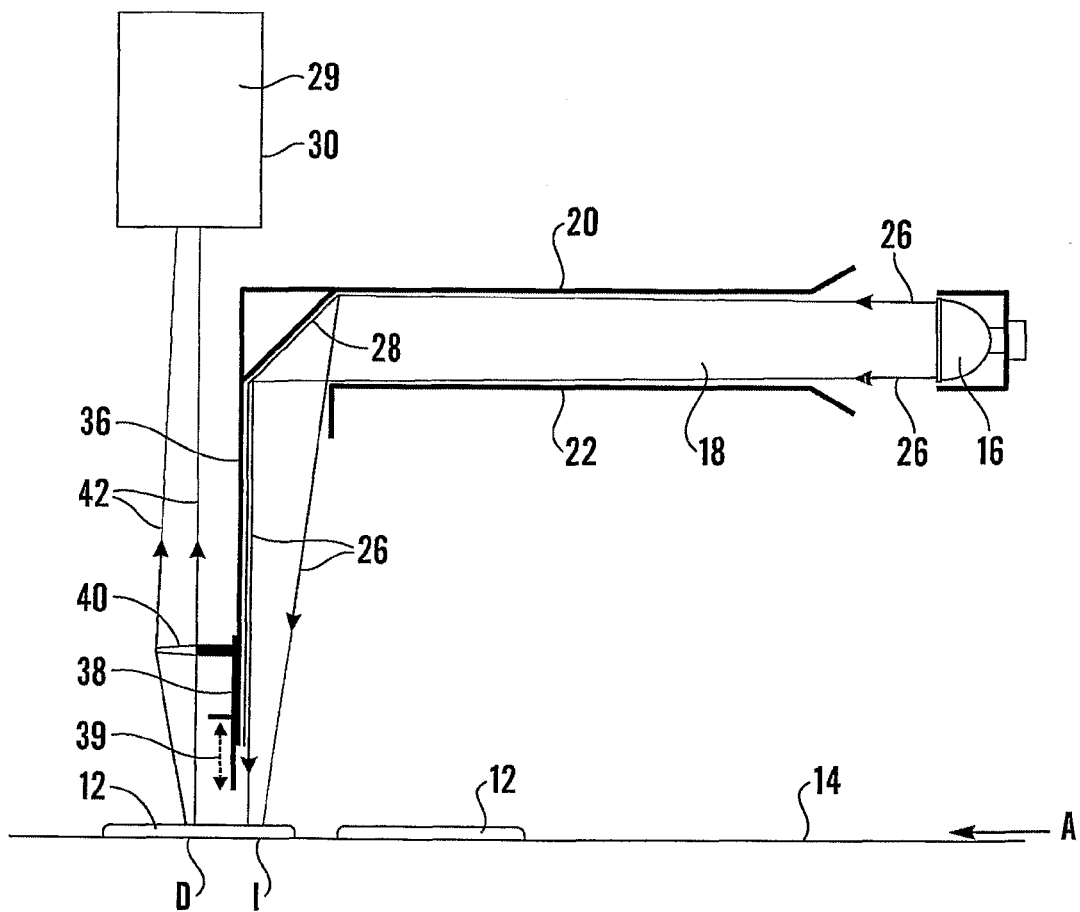

FIG. 1 shows a highly diagrammatic representation of a system for emitting radiation and measuring transflected such radiation, FIG. 2 illustrates diagrammatically, in perspective view from above, a system for automatic inspection of matter utilising transflection, and FIG. 3 shows a diagrammatic vertical section through a modified version of the system of FIG. 2.

Referring to FIG. 1, the system shown comprises a probe 1 including an emitting device 2 which emits a detection medium in the form of beams B of electromagnetic radiation of a substantially constant intensity which are incident to some matter 4, which has a variety of lamina variations within its body. Once the incident beams B reach the surface of the matter 4, some of the radiation penetrates the surface of the matter 4 and is scattered within the matter 4 and varied by the lamina variations within the matter 4. The scattered varied medium then passes out of the matter 4 through the top surface as rays R, a portion of which rays are focussed using an optical arrangement 6, for example a lens, onto a detection device 8 for generating detection data in dependence upon the varied radiation R. The detection device 8 detects wavelengths within the range of wavelengths in the emitted detection medium. The presence of the optical arrangement 6 allows the probe 1 to be located remotely from the matter 4 such that contact between the probe 1 and the matter 4 is not necessary.

Referring to FIGS. 2 and 3, the system 10 is for spectrally assessing matter in the form of split cod samples 12. The cod samples 12 are located skin-side down on a conveyor belt 14 advancing in direction A. The system 10 also includes an emitting device in the form of a row of lamps 16, which are preferably high-intensity, IR-producing, halogen lamps. Alternatively, the emitting means can emit detection medium in the visible wavelength spectrum. The lamps 16 emit detection radiation of a substantially constant intensity into a duct 18 which is bounded by a roof panel 20, a base panel 22 and side wall panels 24, each of these panels being preferably manufactured from blackened metallic plates. Detection medium in the form of radiation beams 26 is channelled horizontally within the duct 18 onto a focussing cylindrical mirror 28, which is preferably a metallic mirror. The beams 26 are directed downwardly by the mirror 28 onto the conveyor belt 14 to form an irradiated zone of substantially constant intensity in the form of an illuminated zone I which continuously extends substantially across the width of the conveyor 14 and thus the stream. The illuminated zone I is preferably as narrow as possible, so as to form on the conveyor belt 14 a relatively thin line of illumination, which thus produces very little stray radiation.

The system 10 may also include, as shown in FIG. 2, a cylindrical polygonal mirror 32 having an axis of rotation R which extends in the direction A and an optical detection device 34. By using the rotary polygonal mirror 32 it is possible to scan the stream of matter 12 along a path D which forms a detection zone which also extends across substantially the whole width of the conveyor belt 14 and thus the stream of matter. Alternatively, an oscillating mirror could be used instead of the rotating polygonal mirror in order to scan the stream of matter along the path D. The detection zone D is, preferably, separated from the illuminated zone I by a distance of 0.5 mm to 10 cm, depending on the matter to be analysed. It is very important to avoid stray radiation reaching the detection zone D from the illuminated zone I since an inherent problem in measuring transflected medium is the low signal-to-noise ratio, so that, if any stray radiation were to reach the detection zone D, for instance reflected radiation from the illuminated zone I, this could cause serious errors in the values obtained. In the present system 10, the suppression of stray radiation is achieved by having a physical light stop in the form of a blackened metallic screen 36, which is attached, at its upper edge, to the roof panel 20 and projects substantially vertically downwardly from the roof panel 20.

The most accurate results when measuring transflected medium are obtained when no diffusely reflected light from the surface(s) of the matter being inspected are received by the detection device. Reflective surfaces will, of course, reflect the detection medium which may cause errors in the detection data, such that the screen 36 becomes very important when inspecting matter with a reflective surface. If the matter being inspected is of a less reflective nature, it is possible, in some instances, that the screen 36 may not be needed.

Alternatively, the system 10 may include a spectral imaging camera 29 having a housing 30 as shown in FIG. 3, instead of the scanning arrangement based on the rotating polygonal mirror 32 and the optical detection device 34 shown in FIG. 2. An arrangement having the spectral imaging camera 29 would include an optical dispersive element (not shown) to allow simultaneous spectral analysis at the detection points along the zone D.

Ideally, the bottom edge of the screen 36 should contact or virtually contact the top surface of the matter 12 passing upon the conveyor 14 to ensure that the maximum amount of stray radiation is suppressed. However, this degree of suppression of stray radiation may not be practical and it is satisfactory if the majority of stray radiation is suppressed.

In order for the transflected medium to be reliably detected, the objects being inspected have to bridge the gap between the illuminated zone I and detection zone D such that analysis of the varied transflected medium occurs substantially simultaneously with irradiation.

Referring specifically to the modified version of the system 10 shown in FIG. 3, the screen 36 has slidably attached to its lower portion an adjustable sub-screen 38 which can be adjusted vertically, as shown by the vertical dashed arrow 39 in FIG. 3, according to the size of the objects passing upon the conveyor 14 and has mounted thereon a cylindrical lens 40.

A number of alternative screen arrangements are possible, for example, the sub-screen 38 can be automatically adaptable to the object sizes in the stream, or the sub-screen 38 can be split into individually adjustable elements, each adjustable element having a lens element attached thereto. The distance between lens(es) 40 and object surface is ideally kept as constant as possible.

Thus, if the matter being advanced by the conveyor 14 is split cod, although relatively flat, an adaptable sub-screen 38 can be advantageous if sizes vary greatly. If not, the sub-screen 38 can be slid downwardly to its lowest allowable position (as shown in FIG. 3) to suppress a sufficient amount of stray radiation.

If the matter being conveyed on the conveyor 14 has a maximum height greater than the distance between the surface of the conveyor 12 and the bottom edge of the sub-screen 38 in its lowest position, then the sub-screen 38 needs to be moved vertically upwardly to allow those items to pass whilst still suppressing a sufficient amount of stray radiation.

The cylindrical lens 40 may be mounted, as shown, on the screen 36 in FIG. 2 and on the sub-screen 38 in FIG. 3 and varied radiation (illustrated by the rays 42 emanating from the matter 12 at the detection zone D) passes through the lens 40 which converges the rays 42 onto the rotary polygonal mirror 32 or onto the spectral imaging camera 29 shown in FIG. 3. The near infrared (NIR) part of the radiation being directed onto the rotary polygonal mirror 32 can then be directed to the detection device 34 for analysis to determine the necessary quality being measured, such as the water content of the split cod.

Advantageously, a further cylindrical lens (not shown), or alternatively a diffractive lens, can be used to focus the beams of the emitted detection medium to a better defined, i.e. narrower, illumination zone I. Preferably, this further lens can be mounted on the screen 36 or sub-screen 38 on the opposite side to that of the lens 40 so that the focussing distance is maintained if the screen is moved. If the screen is not used, it may be important that such a further lens be utilised. Fixing this further lens to the screen ensures a relatively constant distance to the matter.

In use, as the split cod 12 moves along the conveyor 14 it passes through the illuminated zone I at which point the radiation 26 penetrates the upper surface of the split cod 12 which radiation is then scattered and spread within the body of the cod and is varied by the matter within the cod. Some of the varied radiation then passes out of the upper surface of the cod at the detection zone D and is converged onto the rotary polygonal mirror 32 by the lens 40.

It is possible to replace the rotary polygonal mirror 32 with an optical fibre which scans back-and-forth across the detection zone D and conveys the transflected medium to the detecting device 34.

The detection device 34 advantageously comprises either a beam splitter and optical filter combination or an optical dispersive element and sensor array combination, if a scanning detection arrangement is used as shown in FIG. 2. Alternatively, an optical dispersive element and a two dimensional sensor array combination can be used if a spectral imaging camera is used as shown in FIG. 3, for analysing the transflected radiation in a plurality of wavelengths simultaneously. Alternatively, a camera, or the scanning arrangement shown in FIG. 2, can be combined with suitable illumination at different wavelengths instead of using white light and filters or a dispersive element in front of the detection device. For that purpose, one or more filters can be used at the lamps 16 to allow only certain wavelengths to irradiate the illuminated zone I; for example, a filter wheel can be used to irradiate the illuminated zone I with detection medium of selected wavelengths. Alternatively, suitable light emitting diodes can be used to emit detection medium of the selected wavelengths.

The irradiation of the illuminated zone can be static, as shown in FIGS. 2 and 3 with the lamps 16, or it can be dynamic, such as a scanning illumination. With a scanning illumination arrangement, it would normally be necessary to synchronise the scanning illumination with the scanning of the detection zone. It would thus also be possible to use the same unit for illumination and detection.

The data obtained from the detection device 34 is used to produce a spectral image for assessing the necessary parameters, and, if the stream of matter 12 passing upon the conveyor 14 is discrete objects, as opposed to matter such as fluids and pulp-like material, then it is also desirable to produce a two-dimensional spectral image of the detection zone D, such that measurements of the specific parameter being measured can be performed over a region of interest, namely across the conveyor belt 14.

By using the system 10 as shown in FIG. 3 with static illumination, a spectral image can be obtained by employing a spectral imaging camera, or by combining one or more line-scan cameras with appropriate optical filters so that only desired wavelengths of radiation are detected. This particular arrangement has the advantage of producing a better spectral resolution and it has no moving parts, but in the case of NIR, its disadvantages may be the cost of two-dimensional infrared sensors and a relatively low spatial resolution. In the case of visual spectrum detection elements (sensitivity extendable to 1100 nm), line and matrix elements can yield good resolution at relatively low cost.

The two-dimensional simulation of the detection zone D automatically generates a map of a plurality of distinct measurement points distributed across the zone D and is particularly advantageous for larger discrete objects such as split cod, because an average value for the parameter being measured can be obtained. Furthermore, when imaged, the measurements can be weighted according to a model of the sample and grouped for improved interpretation, for example, corresponding to the sample location patterns used for split cod for manual moisture measurements by complete sample drying. These location patterns for sample taking vary from country to country, and the automatic measurements interpretation can thus be brought into conformity with these sample location patterns.

The detection zone D can also be monitored by a plurality of separate spectral measuring units, such as point spectrometers, each dedicated to a spot in the detection zone. Examples of such spot detection units are simple beam splitter/filter detection units, dispersive elements and detector array combinations, and filter wheel units. Certain diffractive optical elements (DOE's), can also yield a low cost spectral unit. In such a system a single DOE would be dedicated to one of the distinct measurement points distributed across the zone D. A diffractive optical element (DOE) is a passive component that redirects chosen wavelengths of the incoming light to a set of predefined positions on a separate detector or detector array. Instead of having a dedicated point spectrometer to each measurement point, the number of individual spectrometers can be reduced, and by tilting the spectrometer the detector can scan portions of the detection zone D.

It is also possible to use a row or a matrix of discrete silicon detectors together with filters or dispersive elements for detecting specific wavelengths within the visible and NIR spectrum range of frequencies. Silicon detectors can be utilised to detect electromagnetic radiation up to approximately 1100 nm and are particularly suitable for colour, water content and protein content measurements.

As a further alternative to the scanning arrangement involving the rotary polygonal mirror 32, the scanning of the detection zone D could be performed by utilising a fibre optic multiplexer which comprises a dedicated fibre optic for each measurement point distributed across the detection zone D, the fibre optics conveying the varied medium from the respective measurement points sequentially to the detecting device 34.

It may also be advantageous to measure transflected medium also at a second detection zone downstream of the first detection zone D, such that the transflected radiation is measured substantially simultaneously at two different distances from the illuminated zone I. The data obtained from both detection zones can be combined to show the decay in spectral intensity with distance, therefore enabling mapping of the radiation path. This can be achieved in a variety of ways, including using a two-line detector in a scanner, using two spectral imaging cameras (these two alternatives measure the intensity of radiation from two complete detection zones which extend across substantially the width of the conveyor belt 14), or using a line detector, or at least some single detectors, which measure the radiation intensity decay in the conveyor belt direction A.

It can also be useful to combine transflection measurements with reflection measurements, either to improve on the detection of material properties or to measure surface properties of the matter. For example, for fish, it would be possible to measure both water content (through the transflected radiation) and to check on the presence of surface markings, such as blood stains, at the same time (by reflected radiation). This can be achieved in the system 10 by having a second detection unit scanning the illuminated zone I in addition to the transflection detection unit scanning the detection zone D on the opposite side of the screen 36. However, particularly with fish, reflection spectral measurements are not always consistent because they are strongly influenced by surface properties, such as the presence of salt crystals, the scales on the skin and the surface properties of the fins.

In respect of sorting of waste objects and in particular to the sorting of plastics containers, where it is desirable to separate the containers into different colour fractions, the reliable identification of slightly coloured transparent plastics objects can prove problematic. For example, for liquid-containing plastics bottles, there is often, at the sorting stage, some liquid left in the bottle which may interfere with the absorption of radiation having passed through the object. The colour determination may be reliant upon this radiation being reflected from the conveyor belt, which can thus cause erroneous determination. However, measurement of the transflected radiation results in reliable colour and material identification and distinction between slightly coloured plastics and clear plastics.

As discussed with reference to FIG. 1, transflected medium can be useful in detecting lamina variations in the matter, such as detection of nylon "sleeves" (gas barriers) in PET bottles.

Transflected medium can also be used in medical applications, in particular, to non-invasive inspection of the skin and the layers of tissues immediately thereunder. A patient, in a lying down position, may be advanced through the illuminated zone I, as is the case with present body scanning machines. In such an application, a particularly adaptive screen 36 such as that with individually adjustable sub-screens 38 as previously mentioned can be used to shield reflected medium from the illuminated zone I reaching the detection zone D. This is due to large variations not only in patient body size but also in the position which the body can take as it advances through the illuminated zone I. Advantageously, the illumination would be performed by a scanning illumination arrangement using a medically safe laser or several co-linear lasers together to produce a zone I from a very rapidly moving spot traversing back and forth across the stream (i.e. the platform upon which the patient is lying). The laser beam would create a very narrow illuminated zone which may simplify the measurements, be focussing insensitive and reduce the required fit of the screen 36. As previously described with reference to a scanning illumination, a scanning detection arrangement (as that shown in FIG. 2) can be synchronised with the scanning illumination, allowing a single unit to be used for illumination and detection. Examples of such possible medical applications can be analysis of blood oxygenation in a patient, and detection of damaged/abnormal tissue structure below the skin surface.

It is also possible to irradiate the detection zone D itself with electromagnetic radiation for the simultaneous determination of reflected radiation from the detection zone D. The electromagnetic radiation used to irradiate the detection zone can be filtered, with an optical filter device, to remove the transflection wavelength measurement spectrum (which is determined by the electromagnetic radiation irradiating the irradiated zone I).

Detection of transflected medium may be supplemented by further detection of medium emitted from the matter being inspected which is of a different wavelength than that of the detection medium with which it is irradiated. Such medium can be that which is caused by excitation of certain materials from being exposed to the detection medium, such as the detection of luminescence, fluorescence and phosphorescence, which can aid in material identification.

The invention claimed is:

1. Apparatus for automatically inspecting a stream of matter of varying composition, comprising: an emitting device serving to emit electromagnetic radiation of a substantially constant intensity, to an irradiated zone of said stream at which said electromagnetic radiation penetrates a surface of said matter, said irradiated zone extending continuously across substantially the width of said stream, said electromagnetic radiation penetrating said surface and being varied by said matter, a receiving device for receiving the varied electromagnetic radiation emanating from said matter at a detection zone substantially separate from said irradiated zone, a physical light stop serving to isolate said detection zone from said irradiated zone, said physical light stop being a screen comprising one or more adjustable sub-screens distributed across substantially the width of said stream, and a detecting device serving to generate detection data in dependence upon the varied electromagnetic radiation, said matter extends through both said irradiated zone and said detection zone, wherein said detecting device serves to detect the intensity of the electromagnetic radiation emanating from said detection zone of a plurality of selected wavelengths substantially simultaneously and at least the majority of the varied electromagnetic radiation received at said receiving device being that electromagnetic radiation which penetrates said matter and is then scattered by said matter as transflected electromagnetic radiation to be received at said receiving device substantially simultaneously with the emitting of said electromagnetic radiation.

2. Apparatus according to claim 1, wherein said detection zone extends substantially across the width of said stream.

3. Apparatus according to claim 1, wherein said detection zone comprises a multiplicity of individual detection points distributed across substantially the width of said detection zone.

4. Apparatus according to claim 1, wherein said emitting device comprises one or more sources of said electromagnetic radiation arranged to be distributed across said stream.

5. Apparatus according to claim 1, wherein said emitting device is arranged to emit said electromagnetic radiation in the form of a scanning beam which scans said irradiated zone.

6. Apparatus according to claim 1, wherein said emitting device is arranged to emit said electromagnetic radiation in the form of a plurality of scanning beams which are co-linear with each other and which scan said irradiated zone.

7. Apparatus according to claim 1, wherein said emitting means comprises an optical filter device.

8. Apparatus according to claim 1, wherein said emitting device and said receiving device are located on the same side of said stream.

9. Apparatus according to claim 8, wherein said emitting device and said receiving device are located beneath said stream.

10. Apparatus according to claim 1, wherein said matter is advanced through said irradiated zone and said detection zone on a conveyor belt.

11. Apparatus according to claim 1, wherein said matter is advanced through said irradiated zone and said detection zone on a vibrating table.

12. Apparatus according to claim 1, and further comprising one or more cylindrical lenses mounted on said screen.

13. Apparatus according to claim 1, wherein said irradiated zone and said detection zone are separated by a distance of substantially 0.5 mm to substantially 10 cm.

14. Apparatus according to claim 1, wherein said receiving device comprises a polygonal mirror having its reflective edges arranged around an axis of rotation of said polygonal mirror, which axis of rotation is substantially parallel to an advance direction of said stream.

15. Apparatus according to claim 1, wherein said receiving device comprises an oscillating mirror.

16. Apparatus according to claim 1, wherein said detecting device comprises a beam splitter and optical filter combination.

17. Apparatus according to claim 1, wherein said detecting device comprises silicon detectors.

18. Apparatus according to claim 1, wherein said receiving device comprises a spectral imaging camera.

19. Apparatus according to claim 18, wherein said detecting device comprises an optical dispersive element and sensor array combination.

20. Apparatus according to claim 19, wherein said detection zone comprises a multiplicity of individual detection points distributed across substantially the width of said detection zone said apparatus further comprising a multiplicity of optical dispersive elements and sensor array combination, each optical dispersive element being dedicated to one of said multiplicity of individual detection points.

21. Apparatus according to claim 19, wherein said optical dispersive element is a diffractive optical element generating multiple spectra.

22. Apparatus according to claim 1, and further comprising a second detection zone downstream of the first mentioned detection zone.

23. Apparatus according to claim 22, wherein said detecting device is a two-line detecting device.

24. Apparatus according to claim 1, and further comprising a second detecting device for detecting reflected electromagnetic radiation from said irradiated zone.

25. Apparatus according to claim 1, and further comprising a second emitting device serving to emit further electromagnetic radiation to irradiate said detection zone, said second emitting means including an optical filter device for filtering from said further electromagnetic radiation the radiation in the transflection measurement wavelength spectrum, said detecting device serving to determine the intensity of electromagnetic radiation reflected from portions of said stream.

26. Apparatus for automatically inspecting a stream of matter of varying composition, comprising an emitting device serving to emit electromagnetic radiation, of a substantially constant intensity, to an irradiated zone of said stream at which said electromagnetic radiation penetrates a surface of said matter, said irradiated zone extending continuously across substantially the width of said stream, said electromagnetic radiation penetrating said surface and being varied by said matter, a receiving device for receiving the varied electromagnetic radiation emanating from said matter at a detection zone substantially separate from said irradiated zone, and a detecting device serving to generate detection data in dependence upon the varied electromagnetic radiation, at least the majority of the varied electromagnetic radiation received at said receiving device being that electromagnetic radiation which penetrates said matter and is then scattered by said matter as transflected electromagnetic radiation to be received at said receiving device substantially simultaneously with the emitting of said electromagnetic radiation, wherein a physical light stop isolates said detection zone from said irradiated zone, said physical light stop being a screen comprising one or more adjustable sub-screens distributed across substantially the width of said stream.

27. Apparatus according to claim 26, wherein said emitting device is arranged to emit said electromagnetic radiation in the form of a scanning beam which scans said irradiated zone.

28. Apparatus according to claim 26, wherein said emitting device is arranged to emit said electromagnetic radiation in the form of a plurality of scanning beams which are co-linear with each other and which scan said irradiated zone.

29. Apparatus according to claim 26, wherein said irradiated zone and said detection zone are separated by a distance of substantially 0.5 mm to substantially 10 cm.

30. Apparatus according to claim 26, and further comprising a second detection zone downstream of the first mentioned detection zone.

31. Apparatus according to claim 26, and further comprising a second detecting device for detecting reflected electromagnetic radiation from said irradiated zone.

32. Apparatus according to claim 26, and further comprising a second emitting device serving to emit further electromagnetic radiation to irradiate said detection zone, said second emitting means including an optical filter device for filtering from said further electromagnetic radiation the radiation in the transflection measurement wavelength spectrum, said detecting device serving to determine the intensity of electromagnetic radiation reflected from portions of said stream.

33. Apparatus for automatically inspecting a stream of matter of varying composition, comprising: an emitting device serving to emit electromagnetic radiation, of a substantially constant intensity, to an irradiated zone of said stream at which said electromagnetic radiation penetrates a surface of said matter, said irradiated zone extending continuously across substantially the width of said stream, said electromagnetic radiation penetrating said surface and being varied by said matter, a receiving device for receiving the varied electromagnetic radiation emanating from said matter at a detection zone substantially separate from said irradiated zone, and a detecting device serving to generate detection data in dependence upon the varied electromagnetic radiation, at least the majority of the varied electromagnetic radiation received at said receiving device being that electromagnetic radiation which penetrates said matter and is then scattered by said matter as transflected electromagnetic radiation to be received at said receiving device substantially simultaneously with the emitting of said electromagnetic radiation, wherein a physical light stop isolates said detection zone from said irradiated zone, said physical light stop being a screen comprising one or more cylindrical lenses mounted thereon.

34. Apparatus according to claim 33, wherein said emitting device is arranged to emit said electromagnetic radiation in the form of a scanning beam which scans said irradiated zone.

35. Apparatus according to claim 33, wherein said emitting device is arranged to emit said electromagnetic radiation in the form of a plurality of scanning beams which are co-linear with each other and which scan said irradiated zone.

36. Apparatus according to claim 33, wherein said irradiated zone and said detection zone are separated by a distance of substantially 0.5 mm to substantially 10 cm.

37. Apparatus according to claim 33, and further comprising a second detection zone downstream of the first mentioned detection zone.

38. Apparatus according to claim 33, and further comprising a second detecting device for detecting reflected electromagnetic radiation from said irradiated zone.

39. Apparatus according to claim 33, and further comprising a second emitting device serving to emit further electromagnetic radiation to irradiate said detection zone, said second emitting means including an optical filter device for filtering from said further electromagnetic radiation the radiation in the transflection measurement wavelength spectrum, said detecting device serving to determine the intensity of electromagnetic radiation reflected from portions of said stream.

40. Apparatus for automatically inspecting a stream of matter of varying composition, comprising: an emitting device serving to emit electromagnetic radiation of a substantially constant intensity, to an irradiated zone of said stream at which said electromagnetic radiation penetrates a surface of said matter, said irradiated zone extending continuously across substantially the width of said stream, said electromagnetic radiation penetrating said surface and being varied by said matter, a receiving device for receiving the varied electromagnetic radiation emanating from said matter at a detection zone substantially separate from said irradiated zone, a physical light stop serving to isolate said detection zone from said irradiated zone, said physical light stop being a screen with one or more cylindrical lenses mounted on said screen, and a detecting device serving to generate detection data in dependence upon the varied electromagnetic radiation, said matter extends through both said irradiated zone and said detection zone, wherein said detecting device serves to detect the intensity of the electromagnetic radiation emanating from said detection zone of a plurality of selected wavelengths substantially simultaneously and at least the majority of the varied electromagnetic radiation received at said receiving device being that electromagnetic radiation which penetrates said matter and is then scattered by said matter as transflected electromagnetic radiation to be received at said receiving device substantially simultaneously with the emitting of said electromagnetic radiation.

41. A method of automatically inspecting a stream of matter of varying composition, comprising: emitting electromagnetic radiation of a substantially constant intensity, so as to irradiate a zone of said stream, which zone extends continuously across substantially the width of said stream, penetrating a surface of said matter with said electromagnetic radiation at the irradiated zone, wherein said electromagnetic radiation is varied by said matter, receiving at a receiving device substantially simultaneously with said emitting the varied electromagnetic radiation emanating from said matter, said matter extending through both said irradiated zone and said detection zone from which said varied electromagnetic radiation emanates, isolating said irradiated zone from said detecting zone by way of a screen, adjusting one or more sub-screens of said screen in accordance with the size of said matter which passes therebeneath and generating detection data in dependence upon the varied electromagnetic radiation, wherein at least the majority of the varied electromagnetic radiation received at said receiving device being that electromagnetic radiation which penetrates said matter and is then scattered by said matter as transflected electromagnetic radiation to be received at said receiving device substantially simultaneously with the emitting of said electromagnetic radiation, said generating including determining the intensity of electromagnetic radiation emanating from said detection zone in respect of a plurality of selected wavelengths simultaneously.

42. A method according to claim 41, and further comprising receiving, substantially simultaneously with said emitting, varied electromagnetic radiation emanating from a second detection zone downstream of the first-mentioned detection zone.

43. A method according to claim 41, and further comprising emitting further electromagnetic radiation to irradiate said detection zone, filtering from the further electromagnetic radiation the radiation in the transflection measurement wavelength spectrum, said generating further including determining the intensity of electromagnetic radiation reflected from portions of said stream.

44. A method according to claim 41, wherein said electromagnetic radiation is emitted in the form of a scanning beam which scans said irradiated zone.

45. A method according to claim 41, wherein said electromagnetic radiation is emitted in the form of a plurality of scanning beams which are co-linear with each other and which scan said irradiated zone.

46. A method according to claim 41, wherein said emitting comprises sequentially irradiating said irradiated zone with electromagnetic radiation of selected wavelengths.

\* \* \* \* \*